United States Patent [19]

Leonard

[11] 4,062,773

[45] Dec. 13, 1977

[54] HIGH SURFACE TO VOLUME STRUCTURE AND METHOD OF GENERATING SAME

[75] Inventor: Ronald J. Leonard, Harvard, Ill.

[73] Assignee: Baxter Travenol Laboratories, Inc., Deerfield, Ill.

[21] Appl. No.: 609,312

[22] Filed: Sept. 2, 1975

Related U.S. Application Data

[63] Continuation-in-part of Ser. No. 510,326, Sept. 30, 1974, abandoned.

[51] Int. Cl.² .............................................. B01D 29/02
[52] U.S. Cl. ................................. 210/65; 210/351; 210/493 R
[58] Field of Search .................. 55/379; 210/350, 351, 210/352, 356, 440, 493, 497, 65

[56] References Cited

U.S. PATENT DOCUMENTS

| | | | |
|---|---|---|---|
| 1,489,519 | 4/1924 | Chateau | 210/497 X |
| 2,186,440 | 1/1940 | Williams | 210/493 |
| 2,330,625 | 9/1943 | Reppmann | 210/493 X |
| 3,713,875 | 1/1973 | Beyer et al. | 210/490 X |

*Primary Examiner*—Frank A. Spear, Jr.
*Attorney, Agent, or Firm*—Paul C. Flattery; George H. Gerstman

[57] ABSTRACT

A filter assembly and element are disclosed herein for use in filtering biological fluids. The assembly includes a variable volume housing within which is positioned a cylindrically-shaped, high surface area filter. During operation, the housing volume is changed, but the surface area available for filtration remains substantially constant. This permits the filter to be operated with low priming volumes and also to effectively reduce gas bubble entrapment in the filter.

A method of making the element and a method for operating the filter assembly are also disclosed.

13 Claims, 11 Drawing Figures

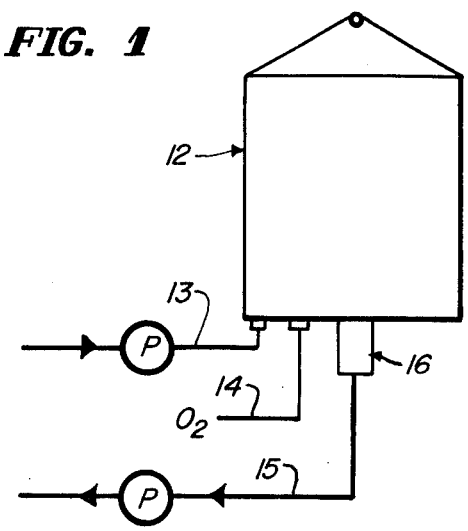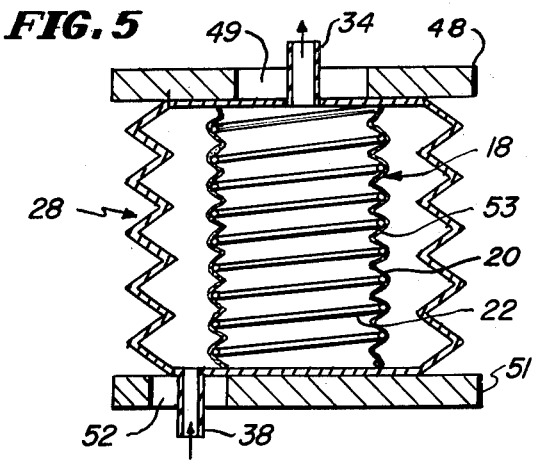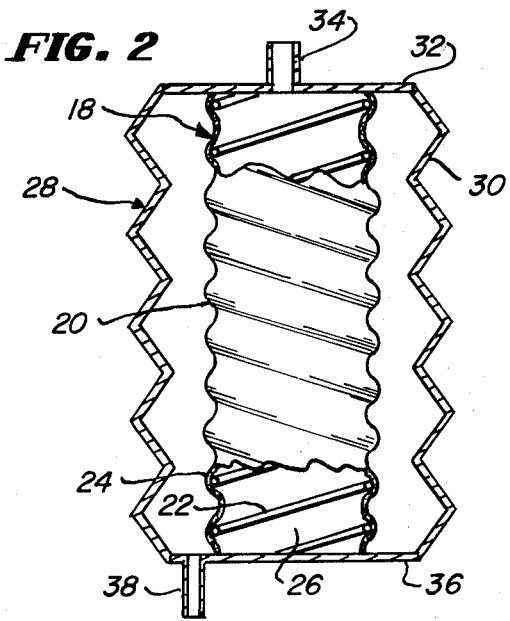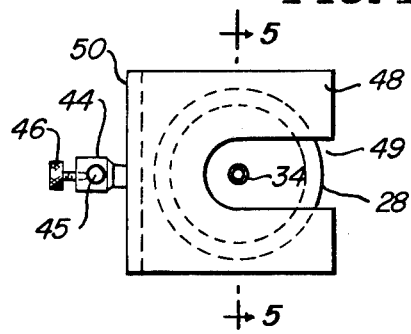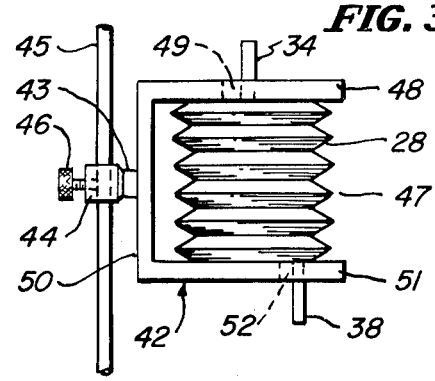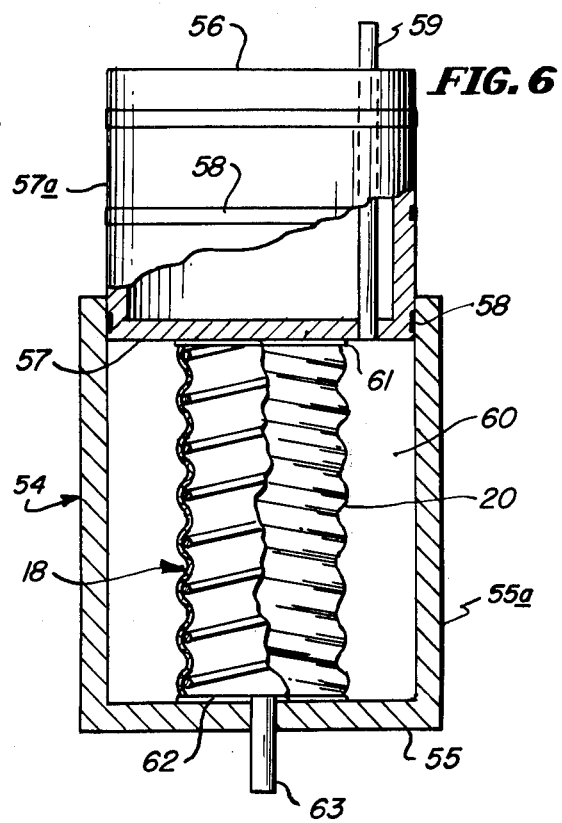

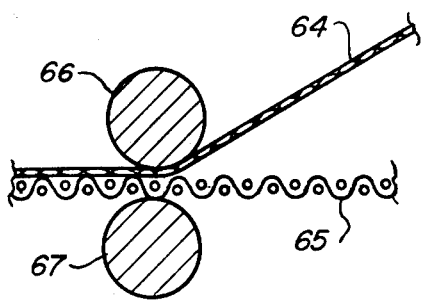
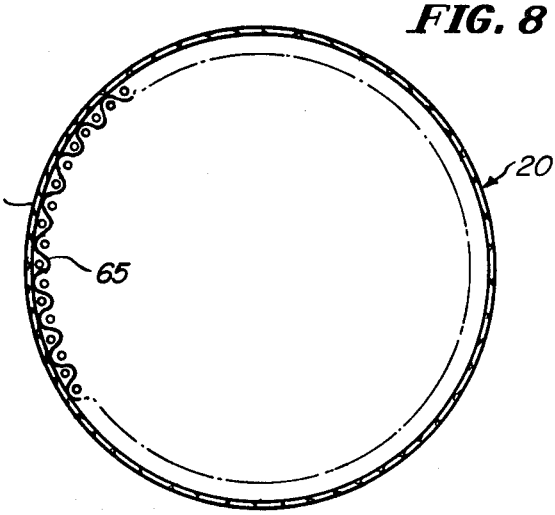
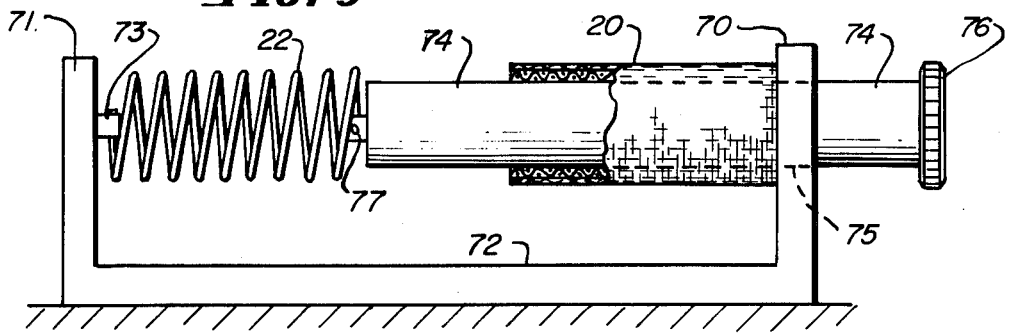
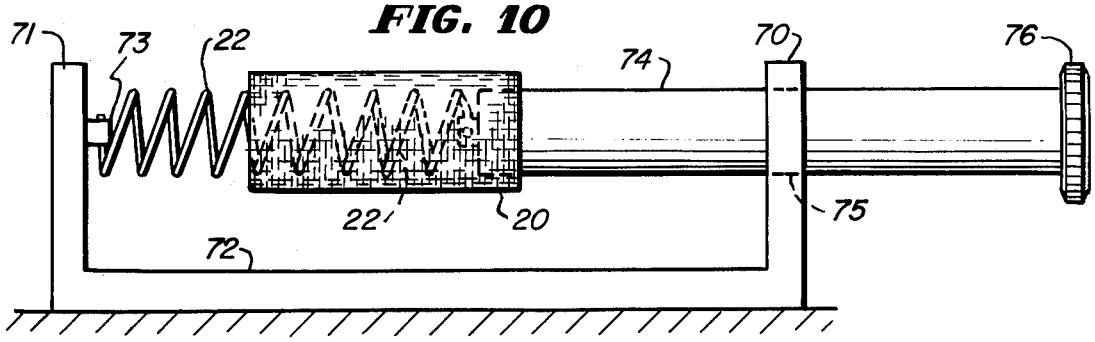
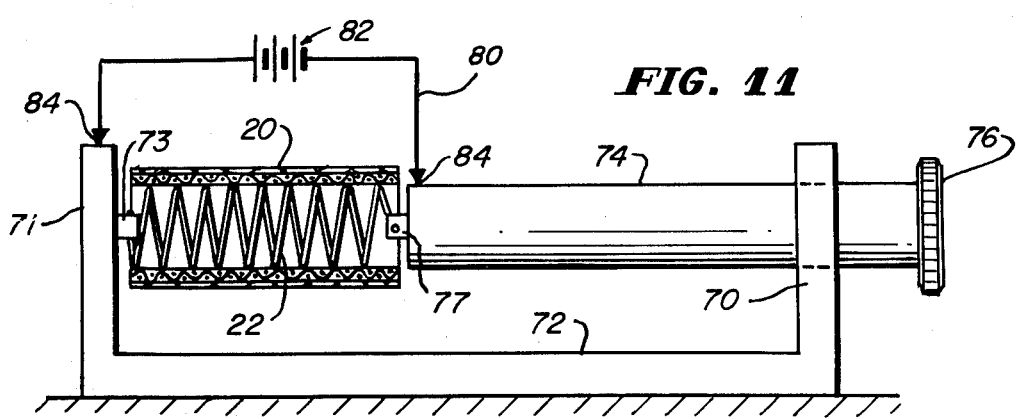

HIGH SURFACE TO VOLUME STRUCTURE AND METHOD OF GENERATING SAME

CROSS REFERENCE TO RELATED APPLICATION

This application is a continuation-in-part of U.S. patent application Ser. No. 510,326 filed Sept. 30, 1974, now abandoned.

BACKGROUND OF THE INVENTION

This invention relates to filter assemblies, and more particularly, to a filter assembly and a filter element for use in filtering blood or other biological fluids.

In blood oxygenator systems, it is desirable to filter oxygenated blood to remove particulate matter before the blood returns to the patient. In such a system, the filter element should have a high surface area in order to provide adequate blood flow rates and high filtration capacity without clogging. On the other hand, the filter assembly should require only a small amount of blood for priming, since it is desirable to minimize the quantity of blood necessary to prime the oxygenator system. Furthermore, the filter assembly should be constructed so as to minimize the entrapment of air bubbles in the filter. The assembly should also be constructed so as to facilitate removal of debris.

Prior art high surface area filters are disclosed in U.S. Pat. Nos. 1,696,313; 2,330,625; and 3,334,748 and French Pat. No. 1.085.481. Such filters are intended for industrial filtration — not medical filtration — and cannot be used for medical filtration inasmuch as they do not provide the combination of features necessary for such use.

It is therefore an object of this invention to provide a filter element and assembly having those features which permit its use as a medical filter that is suitable for use in filtration of blood and other biological fluids.

This and other objects will become apparent from the following description and appended claims.

SUMMARY OF THE INVENTION

There is provided by this invention a filter assembly, and a high surface area filter element, which requires a low priming volume and which can be primed substantially air free. Furthermore, the assembly can be operated in such a manner as to enhance bubble and debris removal.

The filter assembly includes a fluid-tight, variable-volume, housing within which is positioned the filter element. The filter element is a pleated, cylindrical or sleeve-like member having a plurality of circumferential folds. The element includes a coil about which a sleeve of filter material is fitted. The volume of the housing may be varied without changing the surface area available for filtration. The housing is constructed so that it may be compressed or expanded, which simultaneously compresses or expands the filter element, so as to vary the volume of the housing and the filter element without changing the surface area available for filtration.

In operation, the filter assembly is initially expanded during priming so as to fill the assembly with fluid while minimizing the locations at which bubbles can become entrapped and clearing debris from the surface of the element. The assembly is then pumped by suddenly compressing and releasing the housing so as to release or permit to escape any gas bubbles in the fluid within the housing and particularly within the filter element. The filter assembly is then returned to a compressed low-volume position for operation.

The filter element is made by elongating the coil spring so as to reduce its diameter and then slipping a sleeve of laminated filter material thereover. When the spring is released, its diameter increases and the spring engages the filter material so as to form the pleated shape. The sleeve may be bonded to the turns of the spring by electrically heating the spring. The bonding may be enhanced by precoating the spring with polyethylene or polypropylene.

BRIEF DESCRIPTION OF THE DRAWINGS

FIG. 1 is a schematic representation of an oxygenator in a blood circuit which is only partially shown;

FIG. 2 is a side elevational view in section of the filtering assembly of the present invention;

FIG. 3 is a side elevational view of the assembly of FIG. 2, on a reduced scale, mounted on a bracket for holding the assembly in a compressed state;

FIG. 4 is a top plan view of the assembly shown in the view of FIG. 3;

FIG. 5 is a front elevational view in section of the assembly shown in the previous view of FIGS. 3 and 4, but on an enlarged scale;

FIG. 6 is a side elevational view, mostly in section, of a modified embodiment;

FIG. 7 is a schematic sectional representation illustrating a method for forming the filter material;

FIG. 8 is a sectional view, somewhat schematic and on an enlarged scale, of the filter element;

FIG. 9 is a somewhat schematic side elevational view, partly in section, of the apparatus for making the improved filter element, in a first position;

FIG. 10 is a view similar to that of FIG. 9, but showing the apparatus in a second position; and FIG. 11 is a view similar to that of preceding views 9 and 10, but showing the apparatus in a third and final position.

DESCRIPTION OF THE PREFERRED EMBODIMENT

Filter Assembly

Referring now to the drawings, the schematic view of FIG. 1 illustrates a portion of an extracorporeal circuit which includes an oxygenator 12 of the type described in U.S. Pat. No. 3,112,746. An inlet line 13 delivers venous or deoxygenated blood from a patient under urgings of a pump into the oxygenator. An oxygen line 14 delivers oxygen for oxygenating the blood to the oxygenator. An outlet line 15 delivers oxygenated blood under urgings of another pump back to the patient (not shown). An expandable, low-volume, high-surface area filter assembly, shown generally as 16, is provided to remove foreign particulates from the blood. While the filter assembly is shown with an oxygenator, it is to be understood that the assembly can be used for filtering other biological fluids.

One embodiment of the filter assembly is shown in FIG. 2 and includes a housing 28 and an axially-aligned, elongated filter element or body 18. The filter element includes an elongated fluid pervious sleeve member 20 that provides the filtering surface for the element, which is mounted about and shaped by the turns of a coil spring 22. The sleeve member has an outer fine-mesh filter layer 64 of nylon, which is thermally bonded to an inner coarse mesh support layer 65 of extruded polyethylene or polypropylene. Nylon is selected for the outer layer since it is thinner and can be heated for bonding to the polyethylene during laminating.

In the unstressed condition the coil spring 22 has a diameter slightly greater than the sleeve 20, so that when the spring is positioned within the sleeve, it engages the sleeve and shapes the sleeve to provide the pleated filter surface. The sleeve is bonded to the spring along one or more bonding points 24, and such bonding may be enhanced by precoating the spring with polyethylene or polypropylene. Together the sleeve 20 and coil spring 22 provide the filter element which, in turn, defines an inner fluid passageway 26 for fluid entering the element through the sleeve.

The housing member 28 has a bellows-like shape and includes a first or top wall 32, a second or bottom wall 36, and a continuous pleated sidewall 30 to which the top and bottom walls 32, 36 sealingly engage. An outlet 34 is centrally positioned and extends through the top wall 32 and an inlet 38 which extends through the bottom wall is radially offset and positioned adjacent the housing sidewall. The housing member itself can be of a thermoplastic material, such as polyethylene, that is formed by blow molding or the like. The filter element is centrally positioned within the housing and sealingly engages the top wall 32 and bottom wall 36. An annular feed chamber 40, which is the space between the filter element and the housing, communicates with the inlet 38.

The volume of the filter housing, and thus the assembly, is controlled by varying the spacing between the top and bottom walls 32 and 36. During operation, the assembly can be held in a compressed state or position so as to provide the high surface area and low volume filter assembly. One such holding means is a C-shaped bracket 42, as shown in FIG. 3. The C-shaped bracket 42 includes a top plate 48, a bottom plate 51 and an interconnecting back plate 50. The top and bottom plates define an open-front area 47. The top plate 48 includes a top cut-out 49, which is positioned to accommodate the outlet 34 of the housing member 28, and the bottom plate 51 includes a bottom cut-out 52 to accommodate the inlet 38 of the housing member. The bracket 42 also includes a support arm 43 which extends from the back plate 50 and which carries a mounting collar 44, that cooperates with an elongated support or pole 45. A set screw 46 in the collar 44 is arranged to engage the support 45 so as to hold the bracket 42 at selected positions on the support rod.

The sectional view of FIG. 5 illustrates the filter assembly in one compressed position. It is seen that the compressed spring 22 causes the substantially unfolded sleeve member 20 to assume a convoluted configuration having a plurality of marked pleats or folds, one of which is shown as 53. Such folds are formed by convolutions of the unsupported sleeve portions between the turns of the spring, and the unsupported sleeve portions, which are bonded, at least in part, to the spring. It should be noted that such folding does not effect the amount of sleeve or surface area available for filtration. Therefore the amount of area available for filtration is not affected by compressing the filter element, which compression is related to the change in volume of the filter assembly.

Referring now to FIG. 6, there is shown a housing assembly which provides both a housing and a holding means for the filter element 18. The housing includes an open-top, cup-shaped part or cylinder 54 and an open-top part or piston 56, which fits within the cylinder 54. The cylinder 54 includes a bottom wall 55, a sidewall 55a, and a centrally positioned outlet 63, which extends through the bottom wall 55. The piston includes a bottom wall 57, a sidewall 57a and a plurality of annular seals 58 set in the sidewall. An inlet element or tube 59 is positioned within the piston 58 adjacent the sidewall 57a and extends through the bottom wall 57.

The filter element 18 is positioned within the housing between the piston bottom wall and cylinder bottom wall. An upper annular seal 61 is placed between the uppermost turn of the coil spring and piston bottom wall 57, so as to seal the top end of the filter element. A similar lower annular seal 62 is placed between the bottommost turn of the coil spring in the bottom wall 55 of the housing. An annular space or dividing chamber 60, which is defined by the space between the filter element and sidewall 55a, communicates with the inlet 59. The outlet tube 63, which extends through the bottom wall 55 and is positioned to receive fluid flow from the interior of the filter element 18.

Movement of the piston 56 into the cylinder reduces the housing volume and compresses the filter element. The filter element will be maintained in the compressed position, since the coil spring will not overcome the frictional contact of the piston with the cylinder. The sidewall seals 58 increase the frictional forces between the cylinder and housing. If desired, holding means can be associated with the piston to hold the filter element in its compressed condition.

OPERATION

In operation, unfiltered blood or other biological fluids enters the housing through the inlet 38 or 59 and flows into the annular chamber 40 or 60. The fluid then passes through the sleeve portion of the filter element and exits the housing via the outlets 34 or 63. Initially as the blood circuit and filter assembly are being primed, the assembly is expanded so as to fill with blood or biological fluid and reduce the locations at which bubbles can be entrapped. The assembly is then manipulated or pumped to release any trapped gas bubbles in the blood by sudden actions of compressing and releasing of the housing. This pumping action also sheds debris which may have accumulated on the surface of the filter element. After the pumping action, the assembly is compressed to an operating position and held in that position by holding means, such as the C-clamp or by the piston. One advantage of the pleated sidewall of the filter element is that although large particles may become lodged between the folds or against the folds of the sleeve 20, flow around such particles and into the filter element is not disrupted. It will be appreciated that in the embodiments shown, the volume of the assembly and filter element can be varied without affecting the amount of surface area available for filtration.

METHOD OF CONSTRUCTING THE FILTER ELEMENT

Sleeve 20 includes the outer fine mesh filter layer 64, which is made of nylon and the inner coarse mesh support layer 65, which is of polyethylene or polypropylene and which is bonded to the outer layer. The outer layer 64 is preferably a woven nylon mesh material, such as that obtained from Tobler, Ernst & Traber of Switzerland, having a mesh opening of about 20–40 microns along each of its two dimensions and a strand dimension of about 7 microns. The support layer 65 is of a coarser mesh. The two layers are laminated by passing them between a support roller 66 and a heating roller 67, which heat-seals the filtering layer 64 to the support layer 65. The bonded layers are then formed into a cylindrical configuration as shown in the enlarged view of FIG. 8 with the free ends overlapping and heat-sealed.

The filter element is fabricated by mounting the sleeve 20 to the spring 22, as shown in FIGS. 9-11. A mandrel-type fixture is provided which has a pair of spaced upright arms 70 and 71 joined by an elongated base 72. The upright arm 71 has a fixed anchoring lug 73, which secures one final turn or end of the coil spring 22. The upright arm 70 supports movable movable rod 74 which is slidingly fitted into the opening 75. The movable rod has a grasping head 76 at one end, and the opposite end has a movable anchoring lug 77, which secures the other final turn or end of the coil spring 22.

As shown in FIG. 9, the polymeric sleeve 20 is positioned on the movable rod or support 74. In the sequence of steps, the sleeve member is first mounted on the movable support and then a final turn of the spring is secured to the anchoring lug 77. The rod is then moved away from the support arm 71, so that the coil spring is tensioned, elongated and its diameter reduced. The sleeve member 20 has a diameter which is slightly undersized relative to the coil spring at its untensioned state. The coil spring is therefore tensioned until its diameter is reduced sufficiently to allow the sleeve member to be easily slipped over the spring between its opposite turns or ends — such steps being indicated in the view of FIG. 10. After the sleeve is positioned about the coil spring between its opposite ends, the tension of the spring is released by moving the rod 74 towards the upright arm 71. The diameter of the spring thus increases so that the turns bear snugly against the slightly undersized sleeve member. The sleeve member is bonded to the coil spring through heat-seals provided by passing an electric current through the metallic coil spring. The current is provided by a conductor 80 and a voltage source 82, the conductor shown joined to rod 74 and to upright arm 71 by contacts 84. Bonding of the sleeve to the spring may be enhanced by precoating the spring with polylene or polypropylene.

It will be appreciated that numerous changes and modifications can be made to the embodiment shown herein without departing from the spirit and scope of the invention.

What is claimed is:

1. A filter assembly for use in filtering biological fluids which comprises:
   an expandable and contractible bellows-configurated housing having a fluid inlet and a fluid outlet;
   a cylindrically-shaped, high surface area filter element positioned within and cooperatively associated with said housing to filter fluid flowing through said housing between said inlet and said outlet, said filter including an elongated sleeve of filter material and a coil-shaped spring positioned within and engaging said sleeve for shaping said sleeve so as to provide a high surface area for filtration, said filter element being constructed and arranged so that the surface area for filtration remains substantially unchanged as the volume of the housing is changed.

2. A filter assembly as in claim 1, wherein: said filter element is centrally positioned within said housing and an annular chamber is defined by the space between the filter element and the housing; said inlet is positioned to direct unfiltered fluid into said chamber; and said outlet is positioned to receive filtered fluid flow from said filter element.

3. A filter assembly as in claim 2, wherein said housing includes end walls substantially parallel to each other so that the volume of said housing may be varied by moving said end walls toward and away from each other.

4. A filter assembly as in claim 3, wherein said filter element is positioned within said housing, such that one end of the filter element engages one of said end walls and the other engages the other end wall so that said filter element is compressed and expanded as said end walls are moved toward and away from each other.

5. A filter assembly as in claim 4, wherein said inlet extends through one of said end walls.

6. A filter assembly for use in filtering biological fluids which comprises:
   a variable volume housing having: first end wall means; second end wall means; expandable sidewall means, which is adapted to expand and contract upon movement of the end walls toward and away from each other so as to vary the volume of the housing; an inlet; and an outlet; and
   a high surface area filter element positioned within and cooperatively associated with said housing to filter fluid flowing through said housing between said inlet and said outlet, said filter element constructed and arranged so that said surface area for filtration remains substantially unchanged as the volume of the housing is changed.

7. A filter assembly as in claim 6, wherein said filter element is cylindrically shaped and includes:
   a sleeve of filter material; and
   a coil spring positioned within and engaging said sleeve for shaping said sleeve to provide said filtration surface area, with one end of said filter element engaging said first end wall and the other end engaging said second wall so that said filter element is compressed and expanded as said end walls are moved toward and away from each other.

8. A filter assembly as in claim 6, wherein said filter element is centrally positioned within said housing and an annular chamber is defined by the space between the filter element and the housing; said inlet is positioned to direct unfiltered fluid into said annular chamber; and said outlet is positioned to receive filtered fluid flow from said filter element.

9. A filter assembly as in claim 8, wherein said inlet extends through one of said end walls.

10. A filter assembly as in claim 6, wherein said housing sidewalls are bellows shaped.

11. A method for filtering biological fluids in a filter assembly having a variable volume housing with an inlet and an outlet and a filter element having a high surface area, cooperatively associated with said housing and positioned therein to filter fluid flowing between said inlet and said outlet, said filter constructed so that said surface area remains substantially constant as the volume of the housing is changed, said method of filtration including the steps of:
    expanding said housing;
    flowing fluid through said housing through said inlet and outlet so as to fill said housing with fluid;
    pumping said housing so as to remove entrapped gas bubbles; and maintaining said housing in the compressed position during normal operation.

12. A filter element for use in filtering biological fluids which comprises:
   a sleeve of filter material which includes an outer filter layer and an inner support layer bonded to said outer layer;
   coil spring means positioned within and engaging said sleeve for shaping said sleeve so as to provide a high surface area for filtration whether said spring is expanded or compressed;
   said inner support layer being bonded to said shape-sustaining spring; and
   said spring having a coating of polyethylene or polypropylene for cooperation in bonding said spring to said inner layer.

13. A filter element as in claim 12, wherein said outer filter layer is a nylon mesh having openings therein of about 20–40 microns and said inner layer is of polyethylene or polypropylene and has openings therein greater than the openings in said mesh layer.

* * * * *